(12) United States Patent
Gericke et al.

(10) Patent No.: US 9,381,220 B2
(45) Date of Patent: Jul. 5, 2016

(54) SCELETIUM EXTRACT AND USES THEREOF

(71) Applicant: H. L. Hall & Sons Limited, Bryanston (ZA)

(72) Inventors: Nigel Gericke, Noordhock (ZA); Alan Harvey, Glasgow (GB); Alvaro Viljoen, Cresta (ZA); Deon Hofmeyr, Claremont (ZA)

(73) Assignee: H. L. Hall & Sons Limited, Bryanston (ZA)

( * ) Notice: Subject to any disclaimer, the term of this patent is extended or adjusted under 35 U.S.C. 154(b) by 0 days.

(21) Appl. No.: 14/331,962

(22) Filed: Jul. 15, 2014

(65) Prior Publication Data

US 2015/0080447 A1    Mar. 19, 2015

Related U.S. Application Data

(62) Division of application No. 13/256,674, filed as application No. PCT/IB2010/051133 on Mar. 16, 2010, now Pat. No. 8,980,338.

(30) Foreign Application Priority Data

Mar. 20, 2009   (ZA) .................................. 200902001

(51) Int. Cl.
*A61K 36/185* (2006.01)
*A61K 36/40* (2006.01)
*C07D 209/32* (2006.01)
*A61K 31/403* (2006.01)

(52) U.S. Cl.
CPC ............. *A61K 36/185* (2013.01); *A61K 31/403* (2013.01)

(58) Field of Classification Search
None
See application file for complete search history.

(56) References Cited

U.S. PATENT DOCUMENTS

| | | | |
|---|---|---|---|
| 6,271,001 | B1 | 8/2001 | Clarke et al. |
| 6,288,104 | B1 * | 9/2001 | Gericke ................ A61K 31/404 514/421 |
| 8,552,051 | B2 | 10/2013 | Harvey et al. |
| 8,980,338 | B2 | 3/2015 | Gericke et al. |
| 2002/0106731 | A1 | 8/2002 | Ruben et al. |
| 2004/0185429 | A1 | 9/2004 | Kelleher-Andersson et al. |
| 2004/0229291 | A1 | 11/2004 | Zhou et al. |
| 2004/0254152 | A1 | 12/2004 | Monje et al. |
| 2005/0004046 | A1 | 1/2005 | van Praag et al. |
| 2005/0009742 | A1 | 1/2005 | Bertilsson et al. |
| 2005/0009847 | A1 | 1/2005 | Bertilsson et al. |
| 2005/0031538 | A1 | 2/2005 | Steindler et al. |
| 2005/0032702 | A1 | 2/2005 | Eriksson |
| 2012/0004275 | A1 | 1/2012 | Gericke et al. |
| 2012/0041045 | A1 | 2/2012 | Harvey et al. |

FOREIGN PATENT DOCUMENTS

| | | |
|---|---|---|
| DE | 3604112 A1 | 8/1987 |
| WO | 9746234 | 12/1997 |
| WO | 02092112 A1 | 11/2002 |
| WO | 2006025920 A2 | 3/2006 |
| WO | 2010106494 A1 | 9/2010 |
| WO | 2010106495 A1 | 9/2010 |

OTHER PUBLICATIONS

Smith et al. (1998) Pharmaceutical Biology, vol. 36, No. 3, pp. 173-179.*
International Patent Application No. PCT/IB2010/051132, Written Opinion, mailed Jun. 2, 2010, 7 pages.
International Patent Application No. PCT/IB2010/051133, Written Opinion, dated Sep. 2, 2010, 6 pages.
International Patent Application No. PCT/IB2010/051132, International Preliminary Report on Patentability, dated May 19, 2011, 14 pages.
International Patent Application No. PCT/IB2010/051133, International Preliminary Report on Patentability, dated Jun. 27, 2011, 15 pages.
About WordNet, Definition of Prevent, Princeton University <http://wordnet.princeton.edu>, accessed Sep. 18, 2012.
Advisory Action dated Sep. 30, 2013 in related U.S. Appl. No. 13/256,674, 3 pages.
Final Office Action dated Jul. 19, 2013 in related U.S. Appl. No. 13/256,674, 12 pages.
Final Office Action dated Oct. 1, 2014 in related U.S. Appl. No. 13/256,674, 9 pages.
Non-Final Office Action dated Apr. 4, 2014 in related U.S. Appl. No. 13/256,674, 5 pages.
Non-Final Office Action dated Nov. 6, 2012 in related U.S. Appl. No. 13/256,674, 10 pages.
Notice of Allowance dated Dec. 24, 2014 in related U.S. Appl. No. 13/256,674, 9 pages.
Response to Office Action dated May 6, 2013 in related U.S. Appl. No. 13/256,674, 18 pages.

(Continued)

*Primary Examiner* — Chris R Tate
*Assistant Examiner* — Russell Fiebig
(74) *Attorney, Agent, or Firm* — Kilpatrick Townsend & Stockton LLP

(57) ABSTRACT

A composition including as an active ingredient an extract of a plant of the family Mesembryanthemaceae with mesembrenol and mesembrenone as the two major alkaloids present. The invention also relates to the use of the composition as a PDE4 inhibitor and as a serotonin-uptake inhibitor, preferably applied in formulations for the use of the composition as a dual serotonin-uptake inhibitor and PDE4 inhibitor. The invention extends to compositions, such as pharmaceutical compositions or compositions used as dietary supplements, the total alkaloid content of which includes at least 80% (w/w) combined content of mesembrenol and mesembrenone, less than 5% (w/w) mesembrine, and at least 7% (w/w) mesembranol.

17 Claims, 3 Drawing Sheets

(56) References Cited

OTHER PUBLICATIONS

Figure 1:
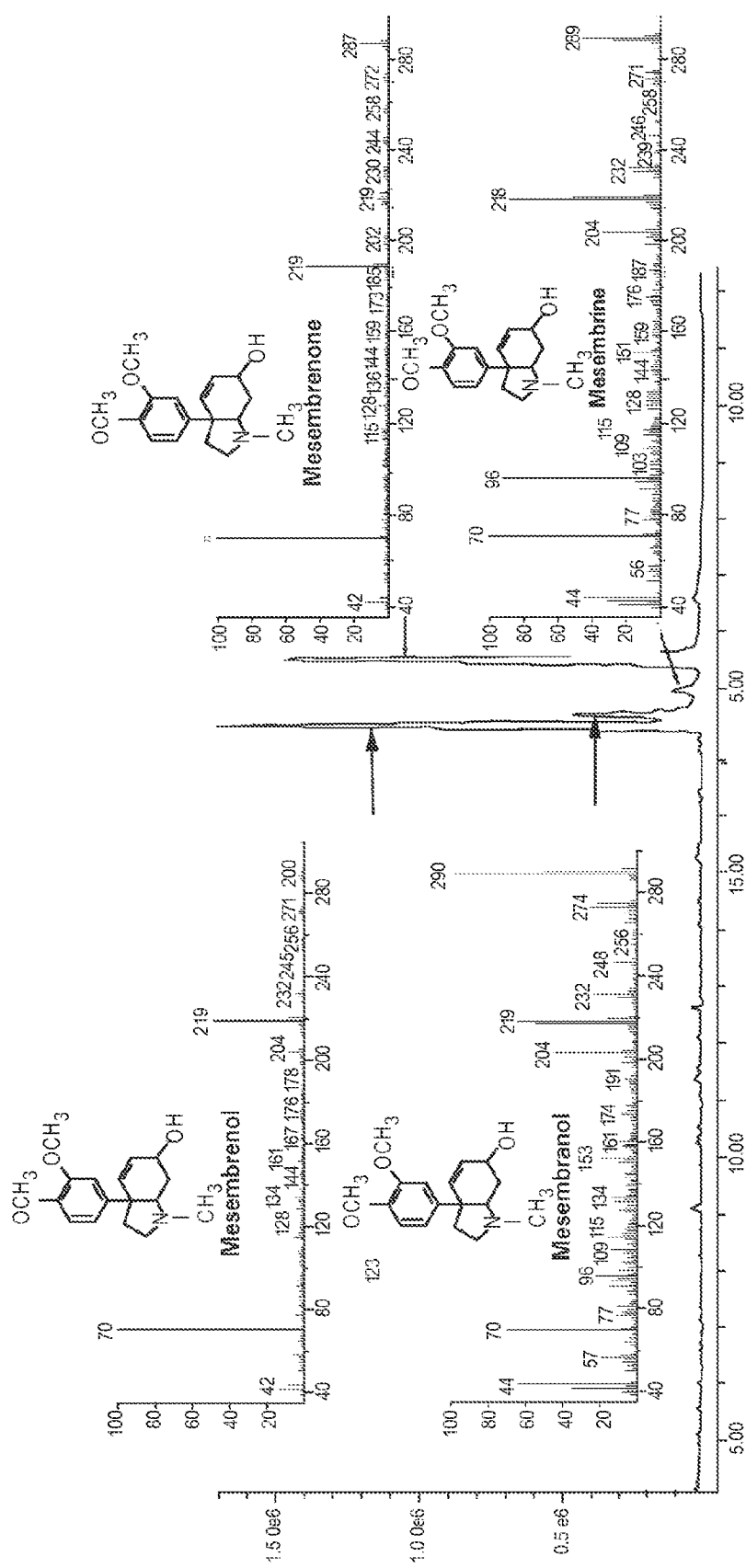

Response to Restriction Requirement dated Aug. 13, 2012 in related U.S. Appl. No. 13/256,674, 14 pages.
Restriction Requirement dated Jun. 13, 2012 in related U.S. Appl. No. 13/256,674, 9 pages.
Non-Final Office Action dated Oct. 23, 2012 in related U.S. Appl. No. 13/256,686, 18 pages.
Notice of Allowance dated Jun. 6, 2013 in related U.S. Appl. No. 13/256,686, 13 pages.
Response to Office Action dated Mar. 25, 2013 in related U.S. Appl. No. 13/256,686, 13 pages.
Gericke, "Sceletium—a review update", Journal of Ethnopharmacology, 119(3), 2008, pp. 653-663.
Harvey, et al., "Pharmacological actions of the South African medicinal and functional food plant Sceletium tortuosum and its principal alkaloids", Journal of Ethnopharmacology, 137(3), Oct. 2011, pp. 1124-1129.
Lang, et al., "Asthma, in Disease Management Project, Cleveland Clinic Center for Continuing Education", http://www.clevelandclinicmeded.com/medicalpubs/diseasemanagementlallergy/bronchial-asthma/>, accessed Oct. 10, 2012.
Napoletano, et al., "Mesembrine is an inhibitor of PDE4 that follows the structure-activity relationship of rolipram", Chemistry Preprint Archive, vol. 2001, Issue 3, Mar. 2001, pp. 303-308.
Patnala, et al., "A capillary zone electrophoresis method for the assay and quality control of mesembrine in Sceletium tablets", Journal of Pharmaceutical and Biomedical Analysis, 48(2), Sep. 2008, pp. 440-446.
Patnala, et al., "Investigations of the phytochemical content of Sceletium tortuosum following the preparation of "Kougoed" fermentation of plant material,", Journal of Ethnopharmacology, 121(1), Jan. 2009, pp. 86-91.
International Search Report dated Jun. 2, 2010 in PCTIB2010/051132.
International Search Report dated Sep. 2, 2010 in PCTIB2010/051133.
Saldou, et al., "Comparison of recombinant human PDE4 isoforms: interaction with substrate and inhibitors", Cell Signal., 10, 1998, pp. 427-440.
Schmeda-Hirschmann, et al., "Activity of Amaryllidaceae alkaloids on the blood pressure of normotensive rates", Pharmacy and Pharmacology Communications, 6(7), 2000, pp. 309-313.
Smith, et al., "Psychoactive Constituents of the Genus Sceletium N.E. Sr. and Other Mesembryanthemaceae", A Review, Journal of Ethnopharmacology, Elsevier Scientific Publishers Ltd., 50(3), 1996, pp. 119-130.
Smith, et al., "The distribution of mesembrine alkaloids in selected taxa of the Mesembryanthemaceae and their modification in the Sceletium derived kougoed", Pharmaceutical Biology, Swets and Zeitlinger, Misse, NL, 36(3), 1998, pp. 173-179.
Tatsumi, et al., "Pharmacological profile of neuroleptics at human monoamine transporters", Eur. J. Pharmacology, 368, 1999, pp. 277-283.
Van Wyke, "A Broad View of Commercially Important Southern African Medicinal Plants", Journal of Ethnopharmacology, 119(3), Oct. 2008, pp. 342-355.
Weniger, et al., "Cytotoxic activity of amaryllidaceae alkaloids", Planta Medica, 61(1), 1995, pp. 77-79.
Zhang, et al., "Phosphodiesterase-4 as a Poental Dug Target", Expert Opinion on Therapeutic Targets, 9(6), Dec. 2005, pp. 1283-1305.
Response to Final Office Action dated Sep. 19, 2013 in related U.S. Appl. No. 13/256,674, 26 pages.
Supplemental Response to Final Office Action dated Sep. 23, 2013 in related U.S. Appl. No. 13/256,674, 3 pages.
Pre-Brief Conference Request dated Oct. 21, 2013 in related U.S. Appl. No. 13/256,674, 11 pages.
Response to Non-Final Office Action dated Jul. 7, 2014 in related U.S. Appl. No. 13/256,674, 11 pages.
Supplemental Response to Non-Final Office Action dated Jul. 10, 2014 in related U.S. Appl. No. 13/256,674, 11 pages.
Response to Final Office Action dated Dec. 1, 2014 in related U.S. Appl. No. 13/256,674, 15 pages.

\* cited by examiner

SCELETIUM EXTRACT AND USES THEREOF

CROSS REFERENCE TO RELATED APPLICATIONS

This application is a divisional of U.S. patent application Ser. No. 13/256,674, filed Mar. 16, 2010, which is the U.S. national phase of International Application No. PCT/IB2010/051133 filed on Mar. 16, 2010 and published in English on Sep. 23, 2010 as International Publication No. WO 2010/106495 A1, which application claims priority to South African Patent Application No. 2009/02001 filed on Mar. 20, 2009. The contents of all of the foregoing applications are incorporated herein by reference.

FIELD OF INVENTION

This invention relates to a composition including as an active ingredient an extract of a plant of the family Mesembryanthemaceae with mesembrenol and mesembrenone as the two major alkaloids present. This invention further relates to the use of the composition as a PDE4 inhibitor, preferably applied in formulations, for the treatment of health conditions amenable to treatment by PDE4 inhibitors, to the use of the composition as a serotonin-uptake inhibitor, preferably applied in formulations, for the treatment of health conditions amenable to the treatment by a serotonin-uptake inhibitor, and to the use of the composition as a dual serotonin-uptake inhibitor and PDE4 inhibitor, preferably applied in formulations, useful for the treatment of conditions amenable to the treatment of dual PDE4/serotonin-uptake inhibitors. The invention further relates to the inclusion of the composition in dietary supplements intended to improve the quality of life of healthy individuals.

BACKGROUND TO THE INVENTION

Plants of the genus *Sceletium* are known to contain an alkaloid content including indole alkaloids such as mesembrenol, mesembranol, mesembrine and mesembranone, the chemical formulae of which are described in U.S. Pat. No. 6,288,104. Plants of the genus *Sceletium* are known to vary widely in terms of the total alkaloid content, as well as the chemistry and relative concentrations of individual *Sceletium* alkaloids (Gericke, N. and A. M. Viljoen. *Sceletium*—a review update. Journal of Ethnopharmacology 119 (2008) 653-663). It is reported that mesembrine is the main active ingredient in Mesembryanthemum tortuosum (van Wyk, B.-E., B. van Oudtshoorn and N. Gericke 2009. Medicinal Plants of South Africa, 2nd Edition, Briza, Pretoria). (Mesembryanthemum tortuosum is a botanical synonym for *Sceletium tortuosum*). It is reported in U.S. Pat. No. 6,288,104 that mesembrine is virtually the only alkaloid present in the leaves of the species *Sceletium tortuosum*. U.S. Pat. No. 6,288,104 describes mesembrine, mesembrenol and mesembranone as having potent 5-HT uptake inhibitory activity and as being useful in treating mental health conditions such as mild to moderate depression. Mesembrine hydrochloride has previously been reported to be a weak PDE4 inhibitor (Napoletano, M. et al. 2001. Mesembrine is an inhibitor of PDE4 that follows the structure-activity relationship of rolipram. Chemistry Preprint Archive, Volume 2001, Issue 3, March 2001, Pages 303-308).

It is generally believed that plants of the genus *Sceletium*, and extracts thereof, should preferably contain high concentrations of mesembrine to contribute substantially to the known biological activity thereof. For bioactive plant extracts intended for human or animal consumption it is desirable to have a reproducible and stable phytochemical profile for the plant material, and for any extract or pharmaceutical composition produced from that plant material. However, mesembrine has been reported to be unstable under a variety of conditions that can occur while harvesting, drying, and extracting the raw material, as well as during storage and formulation of the extract. Mesembrine has been shown to be unstable under conditions of fermentation, exposure to light, exposure to heat, and in an aqueous medium (Patnala, S. and Kanfer, I. Investigations of the phytochemical content of *Sceletium tortuosum* following the preparation of "Kougoed" by fermentation of plant material. J Ethnopharmacol. 2009 Jan. 12; 121(1):86-91).

The applicant has found that it is able to produce a novel composition which may be formulated as a pharmaceutical composition or a dietary supplement, which includes as an active ingredient an extract of a plant of the family Mesembryanthemaceae with mesembrenol and mesembrenone as the two major alkaloids present and having low or trace amounts of mesembrine and a selected minimum amount of mesembranol. The problems associated with stability are alleviated and surprisingly, notwithstanding the low mesembrine content, compositions in accordance with the invention, exhibit potent PDE-4 inhibition properties and retain potent serotonin uptake inhibition properties.

DISCLOSURE OF THE INVENTION

According to a first aspect of the invention there is provided a composition comprising as an active ingredient an extract of a plant or plants from the family Mesembryanthemaceae, the extract including the alkaloids mesembrenol and mesembrenone having a total alkaloid content, and wherein the combined content of mesembrenol and mesembrenone is at least 50% (w/w) of said total alkaloid content.

Preferably, the total alkaloid content of the extract includes a combined content of mesembrenol and mesembrenone greater than 60% (w/w), preferably greater than 70% (w/w), and most preferably greater than 80% thereof.

According to a second aspect of the invention there is provided a composition including as an active ingredient an extract of a plant or plants from the plant family Mesembryanthemaceae, the extract including the alkaloid mesembrine and having a total alkaloid content and wherein the mesembrine content is less than 15% (w/w) of said total alkaloid content.

Preferably, the total alkaloid content of the extract includes a mesembrine content of less than 8% (w/w) of said total alkaloid, more preferably less than 5% (w/w) and even more preferably only trace amounts of mesembrine.

The composition of the invention, e.g. a pharmaceutical composition or a dietary supplement, may therefore include as an active ingredient an extract of the plant family Mesembryanthemaceae, the extract having a total alkaloid content wherein the combined content of mesembrenol and mesembrenone is at least 50% (w/w) of said total alkaloid content and the mesembrine content is less than 15% (w/w) thereof. The plant is preferably a plant from the genus *Sceletium*, more preferably a plant of the species *Sceletium tortuosum* (L.) N.E.Br.

The composition of the invention may further comprise an aqueous or alcoholic extract of the plant which may be in liquid or dry form or a super-critical carbon dioxide extract.

The composition further includes the alkaloid mesembranol. In some embodiments of the invention, the total alkaloid content of the composition may include not less than 1%

(w/w) mesembranol, preferably not less than 5% (w/w), and most preferably not less than 7% (w/w) mesembranol.

Thus, the invention extends to compositions, such as pharmaceutical compositions or compositions used as dietary supplements, the total alkaloid content of which includes at least 80% (w/w) combined content of mesembrenol and mesembrenone, less than 5%(w/w) mesembrine, and at least 7% (w/w) mesembranol.

Each of the 4 alkaloids mentioned above may be used in free form or in the form of an acid addition salt, e.g. obtained by addition of an inorganic or organic acid, e.g. hydrochloride acid salt, preferably a pharmaceutically acceptable addition salt form.

The total alkaloid content of the composition of the invention may be varied by those skilled in the art. Depending on the method of extraction and final concentrations employed by those skilled in the art, this invention extends to extracts where the total alkaloid content of the composition of the invention may be between 0.01% and 100% (by weight), preferably between 0.2% and 0.6% (by weight) thereof, and more preferably between 0.2% and 5.0% (by weight) and most preferably between 0.35% and 0.45% (by weight). The remaining constituents of the composition typically include plant extractives, inactive excipients including but not limited to lactose monohydrate or maltodextrine, or water or ethanol or mixtures thereof.

The composition of the invention may be formulated in the form of a pharmaceutical composition according to a method known in the art, e.g. by mixing with one or more carrier or diluent, e.g. a inactive excipient such as lactose monohydrate.

Preferably the pharmaceutical composition is in unit dosage form. Each unit dose of the pharmaceutical composition may contain 1.0 microgram to 1000 micrograms, preferably 4 micrograms to 200 micrograms of total alkaloids with the alkaloid composition as hereinbefore defined. The pharmaceutical composition may be administered in a unit dose of extract comprising, preferably, a total alkaloid content of 6 to 100 micrograms per dose.

The pharmaceutical composition may be administered by any conventional route, in particular orally, e.g. in the form of aqueous-ethanolic tinctures, tablets, enteric coated tablets, capsules, oral sprays, dissolvable wafers, gums or sub-lingual preparations; nasally, e.g. in the form of nasal sprays, transdermally or topically, e.g. in the form of lotions, creams, ointments or skin patches.

The composition of the invention may be included in or formulated as a dietary supplement which may take the form of a drink, for example teas, flavoured water, fruit juices, soft drinks, energy drinks, dissolvable wafers or food and energy or health bars.

According to yet a further aspect of the invention, there is provided the use of the composition including as an active ingredient an extract of the plant family Mesembryanthemaceae in the manufacture of a medicament for the prevention or treatment of conditions that respond to prevention or treatment with a serotonin uptake inhibitor or a PDE4 inhibitor, or for the prevention or the treatment of conditions that respond to prevention or treatment with a combination of a serotonin uptake inhibitor and a PDE4 inhibitor, the extract having a total alkaloid content wherein the combined mesembrenol and mesembrenone content is at least 50% (w/w) thereof.

According to another aspect of the invention, there is provided the use of the composition including as an active ingredient an extract of the plant family Mesembryanthemaceae in the manufacture of a medicament for the prevention or treatment of conditions that respond to prevention or treatment with a serotonin uptake inhibitor or a PDE4 inhibitor, or for the prevention or treatment of conditions that respond to prevention or treatment with a combination of a serotonin uptake inhibitor and a PDE4 inhibitor, the extract having a total alkaloid content wherein the mesembrine content is less than 15% (w/w) thereof.

In addition to using the composition(s) as hereinbefore described in the manufacture of a medicament for treating diseases or conditions amenable to treatment with a serotonin uptake inhibitor (which include, but are not limited to, mild to moderate depression, psychological and psychiatric disorders where anxiety is present, major depressive episodes i.e. single episode and recurrent depression with associated anxiety, alcohol and drug dependence, bulimia nervosa and in the treatment of obsessive-compulsive disorders), such compositions may be used in the manufacture of medicaments which, on account of their PDE4 inhibitory activity, may also be used for treating diseases or conditions which may respond to treatment by a PDE4 inhibitor, including but not limited to asthma, chronic obstructive pulmonary disease, osteoarthritis, rheumatoid arthritis, allergic rhinitis, eczema and psoriasis, multiple sclerosis, disorders of learning and memory, ulcerative colitis, Parkinson's Disease, and Alzheimers Disease.

The composition has biological activity, in particular as a modulator of PDE4 enzyme activity, and may be used in the treatment of or in the manufacture of a mediciament for the treatment of the following conditions:

Respiratory tract conditions: obstructive diseases of the airways including: asthma, including bronchial, allergic, intrinsic, extrinsic, exercise-induced, drug-induced (including aspirin and NS AID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

Bone and joints conditions: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

Pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

Skin conditions: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

Eye conditions: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

Gastrointestinal tract conditions: glossitis, gingivitis, periodontitis; oesophagitis, including reflux; eosinophilic gastro-enteritis, mastocytosis, Crohn—'s disease, colitis including ulcerative colitis, proctitis, pruritis ani; coeliac disease, irritable bowel syndrome, and food-related allergies which may have effects remote from the gut (for example migraine, rhinitis or eczema);

Abdominal conditions: hepatitis, including autoimmune, alcoholic and viral; fibrosis and cirrhosis of the liver; cholecystitis; pancreatitis, both acute and chronic;

Genitourinary conditions: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvovaginitis; Peyronie's disease; erectile dysfunction (both male and female);

Allograft rejection: acute and chronic following, for example, transplantation of kidney, heart, liver, lung, bone marrow, skin or cornea or following blood transfusion; or chronic graft versus host disease;

CNS conditions: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HTV-associated neuropathies; neurosarcoidosis; central and peripheral nervous system complications of malignant, infectious or autoimmune processes, disorders of cognition, learning and memory, anxiety, depression, Parkinsons Disease.

Other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome; 12. other disorders with an inflammatory or immunological component; including acquired immune deficiency syndrome (AIDS), leprosy, Sezary syndrome, and paraneoplastic syndromes;

Cardiovascular conditions: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

Oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; or, Gastrointestinal tract conditions: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Further, in addition to using the composition(s) of the invention as hereinbefore described in the manufacture of a medicament for treating diseases or conditions amenable to treating with a serotonin uptake inhibitor or to treatment with a PDE4 inhibitor respectively, the composition(s) can be used in the manufacture of a medicament for treating diseases or conditions amenable to treatment with a dual-acting serotonin-uptake and PDE4 inhibitor, including diseases or conditions relating to chronic inflammation and in which anxiety and/or depression are a common associated feature, including for example, but not limited to, asthma, chronic obstructive pulmonary disease, multiple sclerosis, leukaemia, Parkinson's disease, Alzheimer's disease, learning and memory disorders, irritable bowel syndrome, rheumatoid arthritis, osteoarthritis, eczema, and psoriasis.

For the above uses, the required dosage will of course vary depending on the mode of administration, the particular condition to be treated and the effect desired. An indicated unit dosage of the pharmaceutical composition may comprise e.g. a total alkaloid content of 20 micrograms to 200 micrograms, preferably 40 micrograms to 120 micrograms.

The composition may, for example, be administered in accordance with the following regimes wherein the amount of total alkaloid of the composition per unit dose and administration regimens are set out hereunder:

| Anxiety | 100 micrograms in capsule orally 12 hourly |
|---|---|
| mild to moderate depression | 100 micrograms in capsule orally 12 hourly |
| Major depression | 200 micrograms in capsule form 12 hourly |
| Learning and memory in Alzheimers Disease | 100 micrograms to 200 micrograms in capsule form once daily |

Furthermore, the applicant has surprisingly found that unexpectedly low oral doses of the composition enhance the onset of sleep, and the quality of sleep, when taken before retiring to bed at night, and also has stress-relieving activity.

Accordingly, there is also provided for the use of the composition as hereinbefore described in the manufacture of a medicament or supplement for the treatment of sleep disorders, to enhance the onset and quality of sleep in healthy individuals, and for the treatment of, or supportive management of, subjective stress in healthy individuals.

For the above uses, the required dosage will of course vary depending on the mode of administration, and the particular condition to be treated and the effect desired. An indicated unit dosage of the composition may comprise e.g. from 2.0 micrograms to 20 micrograms, preferably 6.0 micrograms to 12 micrograms of the composition.

The composition, which may be included in or formulated as a dietary supplement, may be administered as follows with reference to the amount of total alkaloid per unit dose and administration regimens are set out hereunder: Examples of total doses of alkaloid of the composition included in a dietary supplement are as follows:

| Supports healthy sleep | 6.0 micrograms to 12 micrograms in tincture form orally once at night before retiring |
|---|---|
| Helps maintain emotional equilibrium during emotional stress | 6.0 to 12.0 micrograms in tincture form orally 4 hourly as needed |
| Helps maintain healthy mood | 20 to 40 micrograms in tablet or capsule form once to twice a day |
| Supports healthy memory | 20 to 40 micrograms in tablet or capsule form once to twice a day |

According to a further aspect of the invention there is also provided for a composition, preferably a pharmaceutical composition, e.g. in unit dosage form, as herein before described, for use in the treatment of a condition selected from the group consisting of sleep disorders, mild to moderate depression, psychological and psychiatric disorders where anxiety is present, major depressive episodes, alcohol and drug dependence, bulimia nervosa, and obsessive-compulsive disorders.

According to yet a further aspect of the invention there is provided for a method of treating a patient suffering from a condition selected from the group consisting of sleep disorders, mild to moderate depression, psychological and psychiatric disorders where anxiety is present, major depressive episodes, alcohol and drug dependence, bulimia nervosa, and obsessive-compulsive disorders by administering to the patient a composition, preferably a pharmaceutical composition, e.g. in unit dosage form, as hereinbefore described.

A further non-limiting example is the application of the composition of the invention or a pharmaceutically acceptable salt thereof to conditions of the central and peripheral nervous system that respond to stimulating or increasing neurogenesis, since neuoregenesis is known to be enhanced either by a 5-HT uptake inhibitor or by a PDE4 inhibitor.

Conditions that can be beneficially treated by increasing or stimulating neurogenesis are known in the art (see for example U.S. Patent Application Publication Nos. 20020106731, 2005/0009742 and 2005/0009847, 20050032702, 2005/0031538, 2005/0004046, 2004/0254152, 2004/0229291, and 2004/0185429, herein incorporated by reference in their entirety).

Accordingly, the composition of the invention or a pharmaceutically acceptable salt thereof may be useful in the treatment of diseases characterized by pain, addiction, and/or depression by directly replenishing, replacing, and/or supplementing neurons and/or glial cells and/or enhancing the growth and/or survival of existing neural cells, and/or slowing or reversing the loss of such cells in a neurodegenerative condition.

According to the invention there is provided a method of contacting a neural cell with the composition of the invention or a pharmaceutically acceptable salt thereof in order to increase neurodifferentiation. The method may be used to stimulate a neural cell for proliferation, and thus neurogenesis, via one or more other agents used with the composition of the invention in combination, or to maintain, stabilize, stimulate, or increase neurodifferentiation in a cell or tissue by use of the composition of the invention.

The invention also provides a method comprising contacting the cell or tissue with the composition of the invention or a pharmaceutically acceptable salt thereof. In some embodiments, the cell or tissue is in an animal subject or a human patient as described herein. Non-limiting examples include a human patient treated with chemotherapy and/or radiation, or other therapy or condition which is detrimental to cognitive function; or a human patient diagnosed as having epilepsy, a condition associated with epilepsy, or seizures associated with epilepsy.

Administration of the composition of the invention may be before, after, or concurrent with another condition, or therapy.

Uses of the Composition of the Invention or a Pharmaceutically Acceptable Salt thereof in Neurogenesis Embodiments of the invention include a method of modulating neurogenesis by contacting one or more neural cells with the composition of the invention. The amount of the composition of the invention or a pharmaceutically acceptable salt thereof may be selected to be effective to produce an improvement in a treated subject, or to allow for the detection of neurogenesis in vitro. In some embodiments, the amount is one that also minimizes clinical side effects or drug interactions seen with administration to a subject.

Without being bound by theory, and offered to improve the understanding of the disclosure, phosphodiesterase inhibition is believed to promote neurogenesis by targeting second messenger systems downstream of neurotransmitters and other signaling molecules. Cyclic adenosine monophosphate (cAMP) and cyclic guanosine monophosphate (cGMP) are both examples of such second messengers, and inhibition of PDEs may prolong cAMP and cGMP signals and may increase signaling through neurogenic signal transduction pathways.

Cognitive Function

In other embodiments, and if compared to a reduced level of cognitive function, a method of the invention may be for enhancing or improving the reduced cognitive function or to maintain or stabilize the cognitive function in a subject or patient. The method may comprise administering the composition of the invention to a subject or patient to enhance or improve a decline or decrease of cognitive function due to a therapy and/or condition that reduces cognitive function. In some embodiments, the maintenance or stabilization of cognitive function may be at a level, or thereabouts, present in a subject or patient in the absence of a therapy and/or condition that reduces cognitive function or as a result of a therapy and/or condition that reduces cognitive function.

These methods optionally include assessing or measuring cognitive function of the subject or patient before, during, and/or after administration of the treatment to detect or determine the effect thereof on cognitive function. So in one embodiment, a method may comprise i) treating a subject or patient that has been previously assessed for cognitive function and ii) reassessing cognitive function in the subject or patient during or after the course of treatment. The assessment may measure cognitive function for comparison to a control or standard value (or range) in subjects or patients in the absence of the composition of the invention. This may be used to assess the efficacy of the composition of the invention in alleviating the reduction in cognitive function.

Mood Disorders

In other embodiments, there is provided a method of treating a mood disorder in a subject or patient comprising administering a therapeutically effective amount of the composition of the invention or a pharmaceutically acceptable salt thereof to a subject or patient that is under treatment with a therapy and/or in a condition that results in a mood disorder. Non-limiting examples of mood disorders include depression, anxiety, hypomania, panic attacks, excessive elation, seasonal mood (or affective) disorder, schizophrenia and other psychoses, lissencephaly syndrome, anxiety syndromes, anxiety disorders, phobias, stress and related syndromes, aggression, non-senile dementia, post-pain depression, and combinations thereof.

Identification of Subjects and Patients

The invention includes methods comprising identification of an individual suffering from one or more disease, disorders, or conditions, or a symptom thereof, and administering to the subject or patient a therapeutically effective amount the composition of the invention or a pharmaceutically acceptable salt thereof. The identification of a subject or patient as having one or more diseases, disorders or conditions, or a symptom thereof, may be made by a skilled practitioner using any appropriate means known in the field.

The Subsequent Administration of the Composition of the Invention by the Identification or Diagnosis of a Subject or Patient in Need of One or More Effects Provided by the Composition of the Invention Non-limiting examples of an effect include neurogenic activity and/or potentiation of neurogenesis.

In some embodiments, identification of a patient in need of neurogenesis modulation comprises identifying a patient who has or will be exposed to a factor or condition known to inhibit neurogenesis, including but not limited to, stress, aging, sleep deprivation, hormonal changes (e.g., those associated with puberty, pregnancy, or aging (e.g., menopause), lack of exercise, lack of environmental stimuli (e.g., social isolation), diabetes and drugs of abuse (e.g., alcohol, especially chronic use; opiates and opioids; psychostimulants). In some cases, the patient has been identified as non-responsive to treatment with primary medications for the condition(s) targeted for treatment (e.g., non-responsive to antidepressants for the treatment of depression), and the composition of the invention is administered in a method for enhancing the responsiveness of the patient to a co-existing or pre-existing treatment regimen.

In additional embodiments, the patient in need of neurogenesis modulation suffers from premenstrual syndrome, post-partum depression, or pregnancy-related fatigue and/or depression, and the treatment comprises administering a therapeutically effective amount of the composition of the invention. Without being bound by any particular theory, and offered to improve understanding of the invention, it is believed that levels of steroid hormones, such as estrogen, are increased during the menstrual cycle during and following pregnancy, and that such hormones can exert a modulatory effect on neurogenesis.

In some embodiments, the patient is a user of a recreational drug including but not limited to alcohol, amphetamines, PCP, cocaine, and opiates. Without being bound by any particular theory, and offered to improve understanding of the invention, it is believed that some drugs of abuse have a modulatory effect on neurogenesis, which is associated with depression, anxiety and other mood disorders, as well as deficits in cognition, learning, and memory. Moreover, mood disorders are causative and/or risk factors for substance abuse, and substance abuse (as self-medication) is a common behavioral symptom of mood disorders. Thus, substance abuse and mood disorders may reinforce each other, rendering patients suffering from both conditions non-responsive to treatment. Thus, in some embodiments, the composition of the invention or a pharmaceutically acceptable salt thereof may be used to treat patients suffering from substance abuse and/or mood disorders.

In further embodiments, the patient is on a co-existing and/or pre-existing treatment regimen involving administration of one or more prescription medications having a modulatory effect on neurogenesis. For example, in some embodiments, the patient suffers from chronic pain and is prescribed one or more opiate/opioid medications; and/or suffers from ADD, ADHD, or a related disorder, and is prescribed a psychostimulant, such as ritalin, dexedrine, adderall, or a similar medication which inhibits neurogenesis. Without being bound by any particular theory, and offered to improve understanding of the invention, it is believed that such medications can exert a modulatory effect on neurogenesis, leading to depression, anxiety and other mood disorders, as well as deficits in cognition, learning, and memory. Thus, in some preferred embodiments, the composition of the invention or a pharmaceutically acceptable salt thereof is administered to a patient who is currently or has recently been prescribed a medication that exerts a modulatory effect on neurogenesis, in order to treat depression, anxiety, and/or other mood disorders, and/or to improve cognition.

In additional embodiments, the patient suffers from chronic fatigue syndrome; a sleep disorder; lack of exercise (e.g., elderly, infirm, or physically handicapped patients); and/or lack of environmental stimuli (e.g., social isolation); and the treatment comprises administering a therapeutically effective amount of the composition of the invention or a pharmaceutically acceptable salt thereof.

In more embodiments, the patient is an individual having, or who is likely to develop, a disorder relating to neural degeneration, neural damage and/or neural demyelination.

In further embodiments, a subject or patient includes human beings and animals in assays for behavior linked to neurogenesis. Exemplary human and animal assays are known to the skilled person in the field.

In yet additional embodiments, identifying a patient in need of neurogenesis modulation comprises selecting a population or sub-population of patients, or an individual patient, that is more amenable to treatment and/or less susceptible to side effects than other patients having the same disease or condition. In some embodiments, identifying a patient amenable to treatment with the composition of the invention comprises identifying a patient who has been exposed to a factor known to enhance neurogenesis, including but not limited to, exercise, hormones or other endogenous factors, and drugs taken as part of a pre-existing treatment regimen. In some embodiments, a sub-population of patients is identified as being more amenable to neurogenesis modulation with the composition of the invention or a pharmaceutically acceptable salt thereof by taking a cell or tissue sample from prospective patients, isolating and culturing neural cells from the sample, and determining the effect of the compound on the degree or nature of neurogenesis of the cells, thereby allowing selection of patients for which the therapeutic agent has a substantial effect on neurogenesis. Advantageously, the selection of a patient or population of patients in need of or amenable to treatment with the composition of the invention according to the invention allows more effective treatment of the disease or condition targeted for treatment.

In some embodiments, the patient has suffered a CNS insult, such as a CNS lesion, a seizure (e.g., electroconvulsive seizure treatment; epileptic seizures), radiation, chemotherapy and/or stroke or other ischemic injury. Without being bound by any particular theory, and offered to improve understanding of the invention, it is believed that some CNS insults/injuries leads to increased proliferation of neural stem cells, but that the resulting neural cells form aberrant connections which can lead to impaired CNS function and/or diseases, such as temporal lobe epilepsy. According to the invention, a therapeutically effective amount of the composition of the invention or a pharmaceutically acceptable salt thereof is administered to a patient who has suffered, or is at risk of suffering, a CNS insult or injury to stimulate neurogenesis. Advantageously, stimulation of the differentiation of neural stem cells with the composition of the invention, optionally in combination with one or more other neurogenic agents, activates signalling pathways necessary for progenitor cells to effectively migrate and incorporate into existing neural networks or to block inappropriate proliferation.

Opiate or Opioid Based Analgesic

Additionally, the invention provides for the application of the composition of the invention or a pharmaceutically acceptable salt thereof to treat a subject or patient for a condition due to the anti-neurogenic effects of an opiate or opioid based analgesic. In some embodiments, the administration of an opiate or opioid based analgesic, such as an opiate like morphine or other opioid receptor agonists, to a subject or patient, results in a decrease in, or inhibition of, neurogenesis. The administration of the composition of the invention with an opiate or opioid based analgesic would reduce the anti-neurogenic effect. One non-limiting example is administration of such a combination with an opioid receptor agonist after surgery (such as for treating post-operative pain).

Accordingly there is provided a method of treating post operative pain in a subject or patient by combining administration of an opiate or opioid based analgesic with the composition of the invention or a pharmaceutically acceptable salt thereof.

Other embodiments include a method to treat or prevent decreases in, or inhibition of, neurogenesis in other cases involving use of an opioid receptor agonist, comprising administering a therapeutically effective amount of the composition of the invention or a pharmaceutically acceptable salt thereof as described herein. Non-limiting examples include cases involving an opioid receptor agonist, which decreases or inhibits neurogenesis, and drug addiction, drug rehabilitation, and/or prevention of relapse into addiction. In some embodiments, the opioid receptor agonist is morphine, opium or another opiate.

In further embodiments, the invention includes a method to treat a cell, tissue, or subject which is exhibiting decreased neurogenesis or increased neurodegeneration. In some cases, the cell, tissue, or subject is, or has been, subjected to, or contacted with, an agent that decreases or inhibits neurogenesis. One non-limiting example is a human subject that has been administered morphine or other agent which decreases or inhibits neurogenesis. Non-limiting examples of other agents include opiates and opioid receptor agonists, such as mu receptor subtype agonists, that inhibit or decrease neurogenesis.

Thus in additional embodiments, the methods may be used to treat subjects having, or diagnosed with, depression or other withdrawal symptoms from morphine or other agents which decrease or inhibit neurogenesis. This is distinct from the treatment of subjects having, or diagnosed with, depression independent of an opiate, such as that of a psychiatric nature, as disclosed herein. In further embodiments, the method may be used to treat a subject with one or more chemical addictions or dependencies, such as with morphine or other opiates, where the addiction or dependency is ameliorated or alleviated by an increase in neurogenesis.

The amount of the composition of the invention or a pharmaceutically acceptable salt thereof may be such that it results in a measurable relief of a disease condition like those described herein. As a non-limiting example, an improvement in the Hamilton depression scale (HAM-D) score for depression may be used to determine (such as quantitatively) or detect (such as qualitatively) a measurable level of improvement in the depression of a subject.

Non-limiting examples of symptoms that may be treated according to the invention herein include abnormal behavior, abnormal movement, hyperactivity, hallucinations, acute delusions, combativeness, hostility, negativism, withdrawal, seclusion, memory defects, sensory defects, cognitive defects, and tension. Non-limiting examples of abnormal behavior include irritability, poor impulse control, distractibility, and aggressiveness. Outcomes from treatment according to the invention include improvements in cognitive function or capability in comparison to the absence of treatment.

Additional examples of diseases and conditions treatable by the method according to the invention include, but are not limited to, neurodegenerative disorders and neural disease, such as dementias (e.g., senile dementia, memory disturbances/memory loss, dementias caused by neurodegenerative disorders (e.g., Alzheimer's, Parkinson's disease or disorders, Huntington's disease (Huntington's Chorea), Lou Gehrig's disease, multiple sclerosis, Pick's disease, Parkinsonism dementia syndrome), progressive subcortical gliosis, progressive supranuclear palsy, thalmic degeneration syndrome, hereditary aphasia, amyotrophic lateral sclerosis, Shy-Drager syndrome, and Lewy body disease; vascular conditions (e.g., infarcts, hemorrhage, cardiac disorders); mixed vascular and Alzheimer's; bacterial meningitis; Creutzfeld-Jacob Disease; and Cushing's disease.

The disclosed embodiments also provide for the treatment of a nervous system disorder related to neural damage, cellular degeneration, a psychiatric condition, cellular (neurological) trauma and/or injury (e.g., subdural hematoma or traumatic brain injury), toxic chemicals (e.g., heavy metals, alcohol, some medications), CNS hypoxia, or other neurologically related conditions. In practice, the disclosed methods may be applied to a subject or patient afflicted with, or diagnosed with, one or more central or peripheral nervous system disorders in any combination. Diagnosis may be performed by a skilled person in the applicable fields using known and routine methodologies which identify and/or distinguish these nervous system disorders from other conditions.

Non-limiting examples of nervous system disorders related to cellular degeneration include neurodegenerative disorders, neural stem cell disorders, neural progenitor cell disorders, degenerative diseases of the retina, and ischemic disorders. In some embodiments, an ischemic disorder comprises an insufficiency, or lack, of oxygen or angiogenesis, and non-limiting example include spinal ischemia, ischemic stroke, cerebral infarction, multi-infarct dementia. While these conditions may be present individually in a subject or patient, the disclosed methods also provide for the treatment of a subject or patient afflicted with, or diagnosed with, more than one of these conditions in any combination.

Non-limiting embodiments of nervous system disorders related to a psychiatric condition include neuropsychiatric disorders and affective disorders. As used herein, an affective disorder refers to a disorder of mood such as, but not limited to, depression, post-traumatic stress disorder (PTSD), hypomania, panic attacks, excessive elation, bipolar depression, bipolar disorder (maniac-depression), and seasonal mood (or affective) disorder. Other non-limiting embodiments include schizophrenia and other psychoses, lissencephaly syndrome, anxiety syndromes, anxiety disorders, phobias, stress and related syndromes (e.g., panic disorder, phobias, adjustment disorders, migraines), cognitive function disorders, aggression, drug and alcohol abuse, drug addiction, and drug-induced neurological damage, obsessive compulsive behavior syndromes, borderline personality disorder, non-senile dementia, post-pain depression, post-partum depression, and cerebral palsy.

Examples of nervous system disorders related to cellular or tissue trauma and/or injury include, but are not limited to, neurological traumas and injuries, surgery related trauma and/or injury, retinal injury and trauma, injury related to epilepsy, cord injury, spinal cord injury, brain injury, brain surgery, trauma related brain injury, trauma related to spinal cord injury, brain injury related to cancer treatment, spinal cord injury related to cancer treatment, brain injury related to infection, brain injury related to inflammation, spinal cord injury related to infection, spinal cord injury related to inflammation, brain injury related to environmental toxin, and spinal cord injury related to environmental toxin.

Non-limiting examples of nervous system disorders related to other neurologically related conditions include learning disorders, memory disorders, age-associated memory impairment (AAMI) or age-related memory loss, autism, learning or attention deficit disorders (ADD or attention deficit hyperactivity disorder, ADHD), narcolepsy, sleep disorders and sleep deprivation (e.g., insomnia, chronic fatigue syndrome), cognitive disorders, epilepsy, injury related to epilepsy, and temporal lobe epilepsy.

Other non-limiting examples of diseases and conditions treatable by a method of the invention includes, but is not limited to, hormonal changes (e.g., depression and other mood disorders associated with puberty, pregnancy, or aging (e.g., menopause)); and lack of exercise (e.g., depression or other mental disorders in elderly, paralyzed, or physically handicapped patients); infections (e.g., HIV); genetic abnormalities (down syndrome); metabolic abnormalities (e.g., vitamin B12 or folate deficiency); hydrocephalus; memory loss separate from dementia, including mild cognitive impairment (MCI), age-related cognitive decline, and memory loss resulting from the use of general anesthetics, chemotherapy, radiation treatment, post-surgical trauma, or therapeutic intervention; and diseases of the of the peripheral nervous system (PNS), including but not limited to, PNS neuropathies (e.g., vascular neuropathies, diabetic neuropathies, amyloid neuropathies, and the like), neuralgias, neoplasms, myelin-related diseases, etc.

The advantages of a dual PDE4 and 5-HT uptake inhibition mechanisms of action include the possibility of using a lower dose to achieve the same therapeutic objective in conditions that respond to both a 5-HT uptake inhibitor, as well as a PDE4 inhibitor, such as conditions that modulate neurogenesis. The use of lower doses of the dual acting the composition of the invention can be expected to have a reduced side-effect profile than single-action pharmaceuticals or medicaments, such as a reduction in the loss of libido commonly found with in 5-HT uptake inhibitors; and a reduction in the nausea and vomiting found with PDE4 inhibitors. The dual action of the pharmaceutical or medicament can be an advantage by reducing the number of medications that have to be taken where there is a relevant co-morbidity. For example arthritis together with depression, Alzheimers together with depression.

For the above uses, the required dosage of the total alkaloid of the composition will of course vary depending on the mode of administration, the particular condition to be treated and the effect desired. An indicated daily dosage of the total alkaloid of the composition in the larger mammal, e.g. humans, is in the range from about 5 micrograms to 5 milligrams, preferably from 20 micrograms to 200 micrograms The composition of the invention may conveniently be administered for example in divided doses up to four times a day or in slow release form. Suitable unit dosage forms comprise from about 5 micrograms to 500 micrograms, preferably 20 micrograms to 100 micrograms of the composition of the invention.

The composition of the invention may be administered in free form or in pharmaceutically acceptable salt form, e.g. as indicated above. Such salts may be prepared by conventional manner and exhibit the same order of activity as the composition of the invention in free form.

The composition of the invention or a pharmaceutically acceptable salt thereof may be formulated in the form of a pharmaceutical composition according to a method known in the art, e.g. by mixing with one or more pharmaceutically acceptable carrier or diluent.

The composition of the invention or a pharmaceutically acceptable salt thereof may be administered by any conventional route, in particular enterally, e.g. orally, e.g. in the form an aqueous-ethanolic tincture, a tablet, capsule, softgel, oral spray, gum, wafer or a sub-lingual preparation, nasally, e.g. in the form of a nasal spray or inhaler, or transdermally, e.g. in the form of a skin patch.

The invention also extends to
  a method of treating a PDE4 responsive disease state in a mammal suffering from or at risk of said disease state, e.g. as indicated above, which comprises administering to said mammal a therapeutically effective amount of a composition, preferably a pharmaceutical composition, as hereinbefore described; or
  a method for preventing or treating conditions that respond to prevention or treatment with a serotonin uptake inhibitor, e.g. as disclosed above, in a mammal in need thereof, comprising administering to said mammal a therapeutically effective amount of a composition, preferably a pharmaceutical composition, as hereinbefore described; or a method for preventing or treating conditions that respond to prevention or treatment with a serotonin uptake inhibitor and a PDE4 inhibitor, e.g. as indicated above, in a mammal in need thereof, which comprises administering to said mammal a therapeutically effective amount of a composition, preferably a pharmaceutical composition, as hereinbefore described.

The invention also extends to a composition e.g. a pharmaceutical composition as hereinbefore described, for use in any of the methods as defined above.

SPECIFIC DESCRIPTION OF THE INVENTION

The invention is now described according to the following non-limiting examples and with reference to the accompanying diagrammatic drawings in which the figures represents the following:

FIG. 1: CG-MS chromatogram of a high combined mesembrenol and mesembrenone composition in accordance with the invention showing the four key alkaloid peaks, annotated with the MS spectra and chemical structure illustration for each peak.

Figure 2:
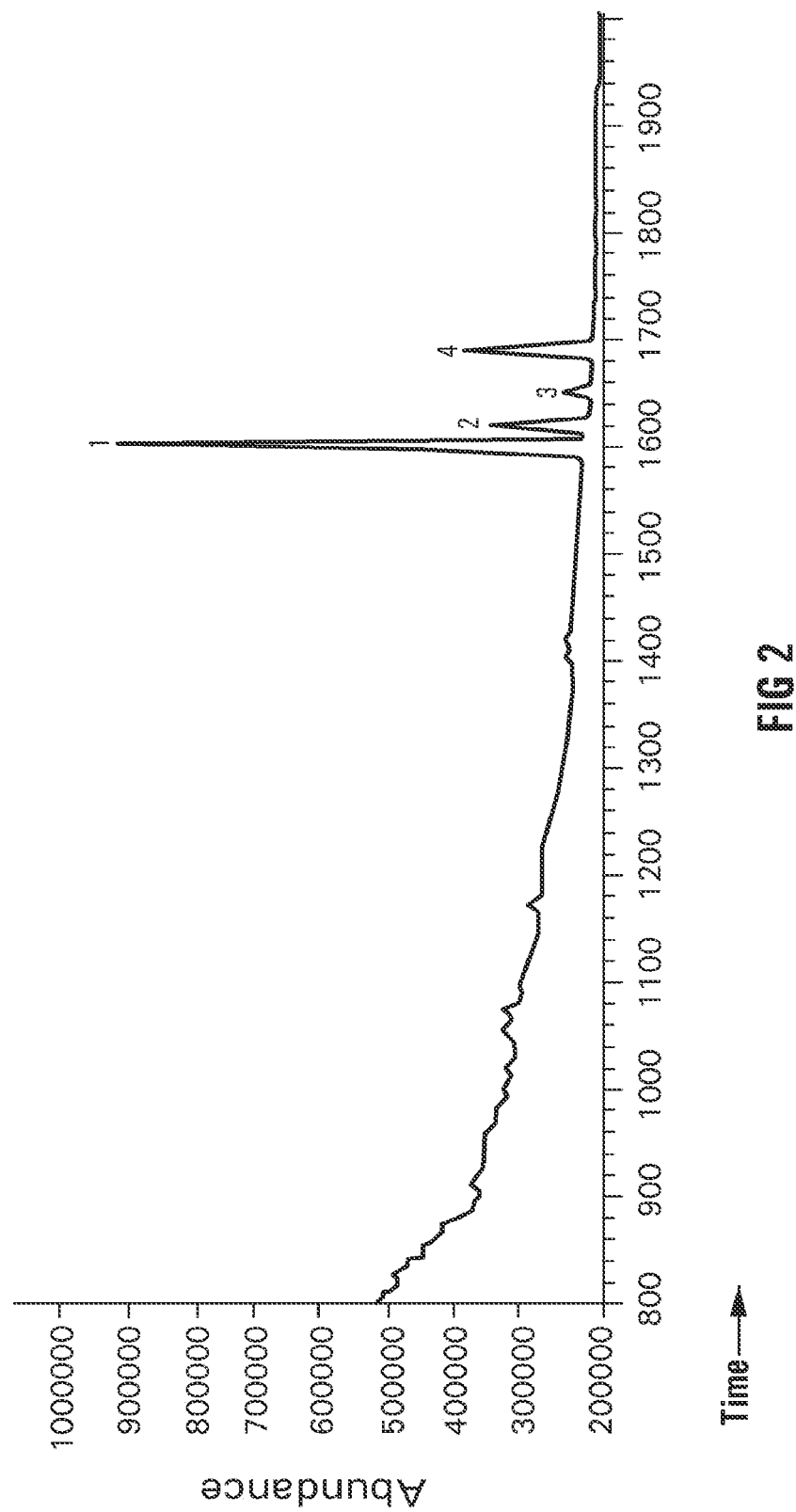

FIG. 2: CG-MS chromatogram and retention times for the key peaks of 4 main alkaloids in the raw material selected for the composition of the invention.

Figure 3:
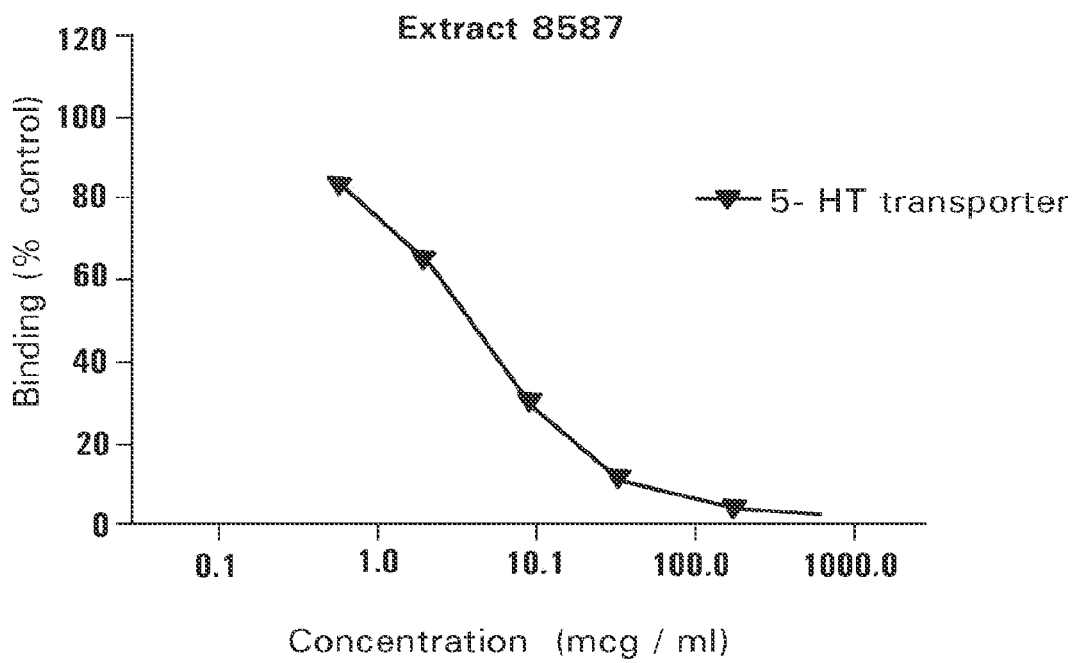
Figure 3:
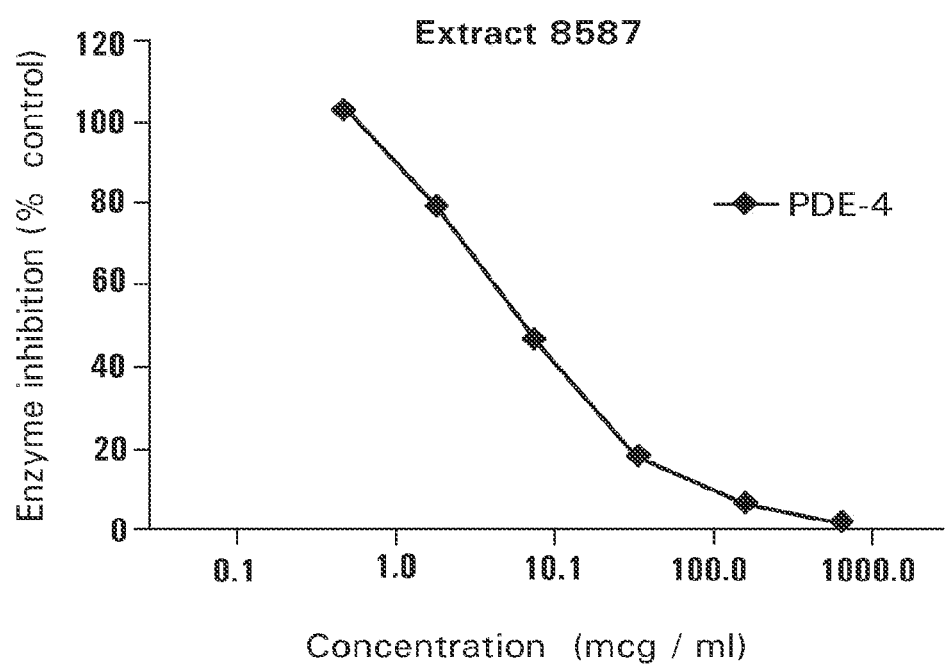

FIG. 3: Concentration-response curves for 5-HT uptake inhibition (top curve) and PDE4 inhibition (bottom curve) of batch 8587 of the composition of the invention.

Raw Plant Material Production

Plant propagation material must first be selected that has the typical alkaloid profile shown in FIG. 2. This is achieved by analysing the individual alkaloid profiles of individual *Sceletium* plants using the method for extraction and GC-MS analysis of alkaloids from *Sceletium* species plant material described below. Plants identified and selected for having the typical total alkaloid profile of high-combined mesembrenol mesembrenone and very low or even trace mesembrine are represented by FIG. 2 and may be kept as propagation material, and also as seed stock. Table 1 below is an example of the alkaloid profiles of 8 individual plants, illustrating that the plants represented by samples TH9 and TH16 would be selected for propagation as they meet the preferred requirements (high combined mesembrenol and mesembrenone, minimum mesembranol, and low-mesembrine) propagation material.

TABLE 1

Examples of relative integration of area of GC-MS peaks for four mesembrine-alkaloids, expressed as a %, for eight individual *Sceletium* plants in commercial production demonstrating the diverse range of mesembrine alkaloid profiles that can be found after targeted selection among cross-pollinated *Sceletium* plant selections under horticultural propagation.

| Plant Sample Number | Mesembrenol + Mesembrenone % | Mesembranol % | Mesembrine % |
|---|---|---|---|
| TH2 | 19.8 | 76.6 | 3.6 |
| TH7 | 95.9 | 0.8 | 3.2 |
| TH9 | 93.9 | 6.2 | Trace |
| TH16 | 96.1 | 3.0 | 0.8 |
| TH23 | 76.4 | 6.4 | 17.2 |
| TH29 | 16.1 | 80.3 | 3.6 |
| DP01 | 24.4 | 20.6 | 55.0 |
| DP02 | 37.6 | 15.0 | 47.5 |

Once selected for having the suitable alkaloid profile, plants can be grown by those skilled in the art from seed, or clonally from conventional rooted cuttings or using conventional tissue-culture propagation. *Sceletium* grows best under intensive and well-managed horticultural conditions. The most reliable biomass production is achieved under conditions of 20-60% shade, with plants grown in individual bags. The soil medium needs to be sterilised for each growing season, and plants correctly spaced to allow for sufficient aeration and to prevent plant diseases. Plants that show any sign of infection must be removed immediately.

TABLE 2

Alkaloid profile of eight individual high-combined mesembrenol and mesembrenone containing plants under cultivation. The relative integration of the areas of GC-MS peaks for four mesembrine-alkaloids are expressed as a %.

| Plant Sample Number | Mesembrenol + Mesembrenone % | Mesembranol % | Mesembrine % |
|---|---|---|---|
| 1. | 84.8 | 12.9 | 2.29 |
| TH16 | 96.1 | 3.0 | 0.8 |
| 7. | 87.7 | 8.4 | 3.9 |
| 9. | 89.7 | 6.3 | 4.0 |
| 11. | 92.1 | 5.3 | 2.6 |
| 15. | 95.5 | 3.0 | 1.5 |
| 16. | 94.6 | 2.9 | 2.5 |
| 17. | 87.5 | 7.2 | 5.2 |
| 18. | 87.0 | 8.2 | 4.8 |

Watering regimens are adjusted on a case-by-case basis to achieve maximal biomass production with plant disease prevention. Nutrients are applied by conventional fertigation, and the water supply to the plants must be filtered and treated with ultravioltet light to minimise exposure to plant pathogens via the water source. *Sceletium* grows best under shade conditions in individual bags so that cultural practices can be more carefully controlled.

Harvesting and Drying

Plants are typically harvested from October to December. Irrigation is curtailed to allow for a lower moisture content in the plant to facilitate drying. Harvesting is done by hand by workers wearing suitable protective gloves. Only the aerial parts of the plant are harvested without any flowers or seed capsules. The fresh biomass is first washed in clean water and allowed to dry in the air. It is crushed using rollers and put onto shallow mesh-lined trays which are stacked and placed in a conventional commercial air drying facility designed for drying fruit. The material is dried at 55° C. for 48 hours with a relative humidity of 30%, to a final moisture content of less than 10%.

Extraction

Dry above-ground plant material is milled using a conventional industrial milling machine, for example a hammer mill, with the mesh size adjusted to achieve a particle size preferably greater than 85 microns and less than or equal to 3 mm.

The milled powder is added to an aqueous, or aqueous-ethanolic solution, most preferably consisting of not less than 70% ethanol, in a suitably sized stainless steel container with an electric stirrer. The ratio of raw material to extraction liquid is preferably between 1:5 to 1:7 by weight. The temperature is preferably kept at between 25° C.-50° C. The mixture is stirred slowly and continuously for 24 hours, then filtered through a suitable commercial filter of sufficient fineness to exclude particulate matter. The filtrate is spray-dried using a conventional spray-drier onto suitable pharmaceutically acceptable excipients such as lactose monohydrate. The amount of pharmaceutically acceptable excipient is adjusted by those skilled in the art to ensure a final total alkaloid content of 0.4% FIG. 1 shows the typical CG-MS chromatogram of the extract with three prominent alkaloid peaks for mesembrenol, mesembranone and mesembrenone and a smaller peak for mesembrine. The CG-MS chromatogram has been annotated to show the MS spectra and chemical structures of mesembrenol, mesembranol, mesembrine and mesembrenone.

Using raw material of the specific high-mesembrenol, low-mesembrine selection of *Sceletium* already described herein, the extract profile could be produced by those skilled in the art using other extraction technologies and processes, including but not limited to, vacuum drying of filtrate, supercritical CO2 extraction, membrane extraction technologies, and microwave extraction.

Method of GC-MS Analysis of Alkaloids From *Sceletium* species Plant Material

Dry above-ground plant material from the plant species of the species *Sceletium tortuosum*(L.)N.E.Br is milled to a fine powder using a Russell & Hobbs Blender™ (Model no. 9715) and then sieved using 500 micron mesh sieve (Endcotts Filters LTD, London). A mass of 5 g of the powder is weighed and transferred to a conical flask. A volume of 60 mL, 0.5 N sulphuric acid (AR grade, Merck LTD) is then added to the mixture which is shaken manually to ensure that the pulverized plant material is in suspension and then left undisturbed for 15 min. The mixture is then filtered into a 250 mL separating funnel using MN 615. 125 mm filter paper (Macherey-Nagel, Germany). A volume of 30 mL of 20% (v/v) ammonia (AR grade, Merck LTD) solution is added to the contents of the separating funnel and gently swirled. Universal litmus paper (pH-Fix, 0-14, Macherey-Nagel) is used in this step to ensure that the pH of the flask is greater than 7 (basic).

Alkaloids are extracted from the basic mixture (prepared above) using AR grade dichloromethane (DCM) from Merck LTD. A volume of 35 mL, DCM is added to the flask which is swirled gently. The mixture is allowed to settle and the lower DCM layer is filtered into round-bottomed flasks using MN 615. 125 mm filter paper. The liquid-liquid extraction is carried out twice and the two DCM filtrates are combined and concentrated on a rotary evaporator (Büchi rotavapor R-200, Switzerland) at 40° C., to a volume of approximately 2 mL. The concentrated extract is transferred into weighed 8.0 mL glass vials and then placed in a vacuum oven (Vismara srl scientific equipment-technical service, model Vo 65) at 40° C. and 0.2 bar. The mass of the dry alkaloid extract is calculated and the percentage yield determined using the formula below.

$$\% \text{ Yield} = \frac{\text{Mass of alkaloid extract}}{\text{Mass of powder (5 g)}} \times 100$$

The dried alkaloids extracts are re-suspended in methanol at a concentration of 10 mg/mL. Approximately 20 microliter of each sample is transferred to Agilent vials. These samples are analysed using a GC-MS system (Agilent 6890N GC). Splitless injection (2 µL) is carried out with an auto-injector at 12.54 psi and an inlet temperature of 255° C. The GC-MS system is equipped with a HP-5MS 5% phenyl methyl siloxane column (30 m×250 µm i.d.×0.25 µm film thickness); the oven temperature program starts at 60° C., rising to 255° C. at a rate of 20° C./min and is held for 15 min. Helium is used as carrier gas at a flow rate of 0.7 mL/min. Spectra are obtained on electron impact at 70 eV, scanning from 35 to 550 m/z. The percentage area of each compound is calculated from the integrated peak area on the FID detector. Compound identifications are performed by comparing their mass spectra and the retention indices with authentic standards. A typical CG-MS chromatogram and retention times of the 4 key alkaloids in the raw material selected for the composition of the invention are shown in FIG. 2.

Method for Determining Total Alkaloid Content of the Extract

A mass of 5 g of the dry powdered extract is weighed and transferred to a conical flask. A volume of 60 mL, 0.5 N sulphuric acid (AR grade, Merck LTD) is then added to the mixture which is shaken manually to ensure that the extract is in suspension and then left undisturbed for 15 min. The mixture is then filtered into a 250 mL separating funnel using MN 615. 125 mm filter paper (Macherey-Nagel, Germany). A volume of 30 mL of 20% (v/v) ammonia (AR grade, Merck LTD) solution is added to the contents of the separating funnel and gently swirled. Universal litmus paper (pH-Fix, 0-14, Macherey-Nagel) is used in this step to ensure that the pH of the flask is greater than 7 (basic).

Alkaloids are extracted from the basic mixture (prepared above) using AR grade dichloromethane (DCM) from Merck LTD. A volume of 35 mL, DCM is added to the flask which is swirled gently. The mixture is allowed to settle and the lower DCM layer is filtered into round-bottomed flasks using MN 615. 125 mm filter paper. The liquid-liquid extraction is carried out twice and the two DCM filtrates are combined and concentrated on a rotary evaporator (Büchi rotavapor R-200, Switzerland) at 40° C., to a volume of approximately 2 mL. The concentrated extract are transferred into weighed 8.0 mL glass vials and then placed in a vacuum oven (Vismara srl scientific equipment-technical service, model Vo 65) at 40° C. and 0.2 bar. The mass of the dry alkaloid extract is calculated and the percentage yield determined using the formula below.

$$\% \text{ Yield} = \frac{\text{Mass of alkaloid extract}}{\text{Mass of powder (5 g)}} \times 100$$

Pharmacological Activity

TABLE 3

Analysis of batch number 8587, an extract derived from the preferred selection of plants as previously described herein.

| Total alkaloid content of the extract %(w/w) | Mesembrenol + Mesembrenone % of total alkaloids (w/w) | Mesembranol % of total alkaloids (w/w) | Mesembrine % of total alkaloids (w/w) |
|---|---|---|---|
| 0.4 | 84.8 | 12.5 | Trace |

Applicant has found that in spite of the plant extract having a very low mesembrine concentration (in other words a mesembrine content of less than 15% of the total alkaloid content of the extract by weight, and in fact only a trace of mesembrine in the batch 8587 of *Sceletium* extract tested), in-vitro binding studies on batch number 8587 of the composition reveals potent concentration-dependent 5-HT uptake inhibition (see Table 4) together with concentration-dependant PDE4 inhibition (see Table 5). The results of the tables are presented as a curve in FIG. 3.

TABLE 4

Binding studies[†] on 5-HT transporter for batch number 8587 of the composition. The control compound is imipramine.

| Test concentration of extract batch 8587 (μg/ml) | % of Control Specific Binding |
|---|---|
| 1 | 81.6 |
| 3 | 61.5 |
| 10 | 28.2 |
| 30 | 8.6 |
| 100 | 3.3 |
| 300 | 0.7 |

[†]General Procedures

| Assay | Origin | Reference Compound | Bibliography |
|---|---|---|---|
| 5-HT transporter (h) | human recombinant (CHO cells) | imipramine | Tatsumi et al. (1999)[(A)] |

[(A)]TATSUMI, M., JANSEN, K., BLAKELY, R. D. and RICHELSON, E. (1999) Pharmacological profile of neuroleptics at human monoamine transporters. *Eur. J. Pharmacol.*, 368: 277-283.

Experimental Conditions

| Assay | Ligand | Conc. | Non Specific | Incubation | Method of Detection |
|---|---|---|---|---|---|
| 5-HT transporter (h) | [³H]imipramine | 2 nM | imipramine (10 μM) | 60 min./ 22° C. | Scintillation counting |

Analysis and Expression of Results

The specific ligand binding to the receptors is defined as the difference between the total binding and the nonspecific binding determined in the presence of an excess of unlabelled ligand.

The results are expressed as a percent of control specific binding ((measured specific binding/control specific binding)×100) obtained in the presence of Extract batch#8587.

The $IC_{50}$ values (concentration causing a half-maximal inhibition of control specific binding) and Hill coefficients (nH) were determined by non-linear regression analysis of the competition curves generated with mean replicate values using Hill equation curve fitting ($Y = D + [(A-D)/(1+(C/C_{50})^{nH})]$, where Y=specific binding, D=minimum specific binding, A=maximum specific binding, C=compound concentration, $C_{50} = 10_{50}$, and nH=slope factor).

TABLE 5

PDE 4 inhibition[‡] for batch number 8587 of the composition. The control compound is rolipram.

| Test concentration of extract batch 8587 (μg/ml) | % of Control Specific Enzyme Activity |
|---|---|
| 1 | 100.7 |
| 3 | 77.7 |
| 10 | 43.8 |
| 30 | 17.2 |
| 100 | 4.8 |
| 300 | 0.6 |

[‡]General Procedure

| Assay | Origin | Reference Compound | Bibliography |
|---|---|---|---|
| PDE4B[(h)] | human recombinant (Sf9 cells) | rolipram | Saldou et al. (1998)[(B)] |

[(B)] SALDOU, N., OBERNOLTE, R., HUBER, A., BADCKER, P. A., WILHELM, R., ALVAREZ, R., LI, B., XIA, L., CALLAN, O., SU, C., JARNAGIN, K. and SHELTON, E. R. (1998), Comparison of recombinant human PDE4 isoforms: interaction with substrate and inhibitors. *Cell Signal.*, 10: 427-440.

Experimental Conditions

| Assay | Substrate | Incubation | Reaction Product | Method of Detection |
|---|---|---|---|---|
| PDE4B (h) | cAMP (40 nM) | 30 min./ 22° C. | residual AMPc | HTRF |

Analysis and Expression of Results

The results are expressed as a percent of control specific activity ((measured specific activity/control specific activity)×100) obtained in the presence of Extract batch #8587

The $10_{50}$ values (concentration causing a half-maximal inhibition of control specific activity) and Hill coefficients (nH) were determined by non-linear regression analysis of the inhibition curves generated with mean replicate values using Hill equation curve fitting ($Y = D + [(A-D)/(1+(C/C_{50})^{nH})]$, where Y=specific activity, D=minimum specific activity, A=maximum specific activity, C=compound concentration, $C_{50} = 10_{50}$, and nH=slope factor).

TABLE 6

IC50 and Hill coefficient from the concentration - response curves for batch number 8587 of the composition.

| Assay | IC50 (μg/ml) | Hill coefficient |
|---|---|---|
| 5-HT transporter | 4.3 | 1.1 |
| PDE4 (non-selective) | 8.5 | 1.3 |

The $IC_{50}$'s for the 5-HT transporter and for the PDE4 assays are very close together, indicating that at physiological doses of the composition that achieve 5-HT uptake inhibition, the composition is likely to be operating as a dual 5-HT uptake inhibitor and a PDE4 inhibitor. The Hill coefficient is a measure of the slope of the dose-response curve; when the coefficient is in the region of 1.0, the interaction at the binding site is likely to be competitive.

It can therefore be seen from the above data that the composition of the invention has dual 5-HT uptake inhibitory and PDE4 inhibitory activity.

Accordingly, the Applicants have found that a composition that includes as an active ingredient an extract of a plant of the family Mesembryanthemaceae with mesembrenol and mesembrenone as the major alkaloids present, and whilst having low or trace amounts of mesembrine and selected amounts of mesembranol, shows remarkable serotonin uptake and PDE4 inhibition. This is particularly advantageous in that the composition lends itself to a wider use for medicinal purposes including in formulations for treating inflammatory conditions, and formulations for treating conditions with deficits in learning and memory. A further advantage of the above combination is the dual action of the composition which makes it suitable to treat conditions wherein the conditions of a patient are responsive to PDE4 inhibition, such as chronic inflammatory diseases where anxiety and depression are a common feature. Still a further benefit is that a low-mesembrine composition avoids the poor stability issues associated with mesembrine.

The use of the composition(s) of the invention to treat sleep disturbance and depression is demonstrated below with reference to the following non-limiting examples.

EXAMPLES

Quality of Sleep

N=4

4 healthy adult volunteers with intermittent disturbance in onset of restful sleep and poor quality of sleep.

Each takes a single oral dose of 1.5 mg of the composition fifteen to twenty minutes before retiring at night. No concomitant medication, or dietary supplements are taken.

The dose of the composition is achieved by taking a measured 300 µl of 30% ethanol-water tincture, containing a dissolved concentration of the composition of 5 mg/ml. The composition is extract batch #8587, as heretofore described. (See Table 3) This dose of the composition was taken by each volunteer on at least four separate occasions for the same sleep disturbances.

All four volunteers report a marked positive effect, with rapid onset of sleep, typically within ten to fifteen minutes of taking the dose, and also improved quality and depth of sleep on each occasion the extract is taken.

Antidepressant and Anxiolytic Activity

N=4

4 adult volunteers with moderate to severe depression, with associated anxiety, take a 100 microgram dose of total alkaloid of the composition once to twice a day orally for a duration of 36 months, 24 months, 16 months and 6 months respectively. The composition is extract batch #8587, as heretofore described (See Table 3) filled in size 0 gelatin capsule, together with the conventional excipients dicalcium phosphate and magnesium stearate to make a total capsule weight of 300 mg.

All four volunteers report rapid improvement in mood and marked reduction in anxiety within 24-48 hours of starting the capsules of extract, and note a feeling of markedly reduced stress and tension. No significant side-effects are noted.

The invention claimed is:

1. A composition, in unit dosage form, for reducing one or more conditions selected from the group consisting of anxiety, stress, tension, sleep disturbance, and depression in a patient in need thereof, said composition comprising an effective amount of a *Sceletium tortuosum* extract, wherein the extract contains the alkaloids mesembrenol and mesembrenone, wherein combined content of mesembrenol and mesembrenone is greater than 80% (w/w) of the total alkaloid content in the extract, wherein the content of the alkaloid mesembrine is less than 15% (w/w) of the total alkaloid content in the extract, and wherein the unit dosage form is selected from the group consisting of an aqueous-ethanolic tincture, a tablet, an enteric coated tablet, a capsule, a dissolvable wafer, a lotion, a cream, an ointment, and a skin patch.

2. The composition of claim 1, wherein the mesembrine content in the extract is less than 8% (w/w) of the total alkaloid content.

3. The composition of claim 2, wherein the mesembrine content in the extract is less than 5% (w/w) of the total alkaloid content.

4. The composition of claim 3, wherein the extract includes trace amounts of mesembrine.

5. The composition of claim 1, wherein the extract further includes alkaloid mesembranol, and wherein mesembranol content in the extract is not less than 1% of the total alkaloid content.

6. The composition of claim 5, wherein the mesembranol content in the extract is not less than 5% of the total alkaloid content.

7. The composition of claim 5, wherein the mesembranol content in the extract is not less than 7% of the total alkaloid content.

8. The composition of claim 1, in which the total alkaloid content of the extract is between 0.20% and 0.60% (by weight) of weight of the composition.

9. The composition of claim 8, in which the total alkaloid content of the extract is between 0.20% and 0.50% (by weight) of the weight of the composition.

10. The composition of claim 9, in which the total alkaloid content of the extract is between 0.35% and 0.45% (by weight) of the weight of the composition.

11. The composition of claim 1, wherein the composition inhibits serotonin uptake and PDE-4 activity in the patient.

12. The composition of claim 11, wherein the administration regimen comprises administering a daily dose of the total Mesembrvanthemaceae alkaloid content from 5 micrograms to 5 milligrams.

13. The composition of claim 1, wherein the unit dose of the composition contains 1.0 microgram to 100 micrograms of the total alkaloid content in the extract.

14. The composition of claim 13, wherein the unit dosage form is an oral unit dosage form.

15. The composition of claim 1, wherein the composition further comprises a pharmaceutically acceptable excipient.

16. A method of inhibiting serotonin uptake and PDE4 activity in a patient in need thereof comprising administering to the patient effective amount of the composition of claim 1.

17. The method of claim 16, wherein a daily dose of the administered composition contains a total alkaloid content from 5 micrograms to 5 milligrams.

* * * * *